United States Patent [19]

Guy

[11] 4,286,602
[45] Sep. 1, 1981

[54] TRANSILLUMINATION DIAGNOSTIC SYSTEM

[76] Inventor: Robert Guy, 4, rue de la Charité, Lyons, France, 69002

[21] Appl. No.: 50,329

[22] Filed: Jun. 20, 1979

[51] Int. Cl.³ .................... A61B 5/00; A61B 6/12
[52] U.S. Cl. ................................. 128/665; 128/23
[58] Field of Search ............... 128/664, 665, 666, 23, 128/22; 354/126

[56] References Cited

U.S. PATENT DOCUMENTS

| 3,127,115 | 3/1964 | Yellott et al. ................ 128/23 |
| 3,168,859 | 2/1965 | Mast .......................... 354/126 X |
| 3,371,202 | 2/1968 | Moore et al. ............... 128/23 X |
| 3,385,188 | 5/1968 | Ellman ....................... 354/126 |
| 3,527,932 | 9/1970 | Thomas ....................... 128/23 |
| 3,674,008 | 7/1972 | Johnson ...................... 128/23 |
| 3,711,700 | 1/1973 | Westlund et al. .......... 128/23 X |
| 3,732,416 | 5/1973 | Audesse et al. ........... 128/23 X |
| 3,769,963 | 11/1973 | Goldman et al. .......... 128/665 |
| 4,077,399 | 3/1978 | LeRoy ........................ 128/665 |
| 4,212,306 | 7/1980 | Mahmud ..................... 128/665 |

FOREIGN PATENT DOCUMENTS

| 279879 | 10/1971 | U.S.S.R. ..................... 128/23 |
| 591178 | 2/1978 | U.S.S.R. ..................... 128/665 |

OTHER PUBLICATIONS

Gros et al., *J. Radio Electrol.* 53, 297–1972, "Diaphanologie Mammaire".

Primary Examiner—Kyle L. Howell
Attorney, Agent, or Firm—Michael Ebert

[57] ABSTRACT

A transillumination system for carrying out breast examination to determine the existence of a carcinoma and other pathological conditions. The system includes a portable light-beam projector in the form of a gun which houses a low-voltage, high wattage lamp whose reflector is sealed to the end of the gun barrel to project a light beam therethrough, the gun grip having a trigger-finger switch for the lamp. The gun operates in conjunction with a camera assembly formed by a tripod-mounted bracket having a camera secured to one end, the camera being trained on a guide fixture attached to the other end. The fixture is adapted to engage the rib cage of the patient just above the breast and to present the breast to the camera lens at a fixed location. The shutter mechanism of the camera is coupled to a remote actuator operable by one hand or foot of the operator. Thus an operator who holds the gun in his hand is able without assistance to orient the light beam relative to the patient's breast and to activate the trigger finger switch to transilluminate and observe the internal structure of interest, the operator also being in a position to take a well-focused picture of the transilluminated breast without having to observe the image through the range finder of the camera.

8 Claims, 6 Drawing Figures

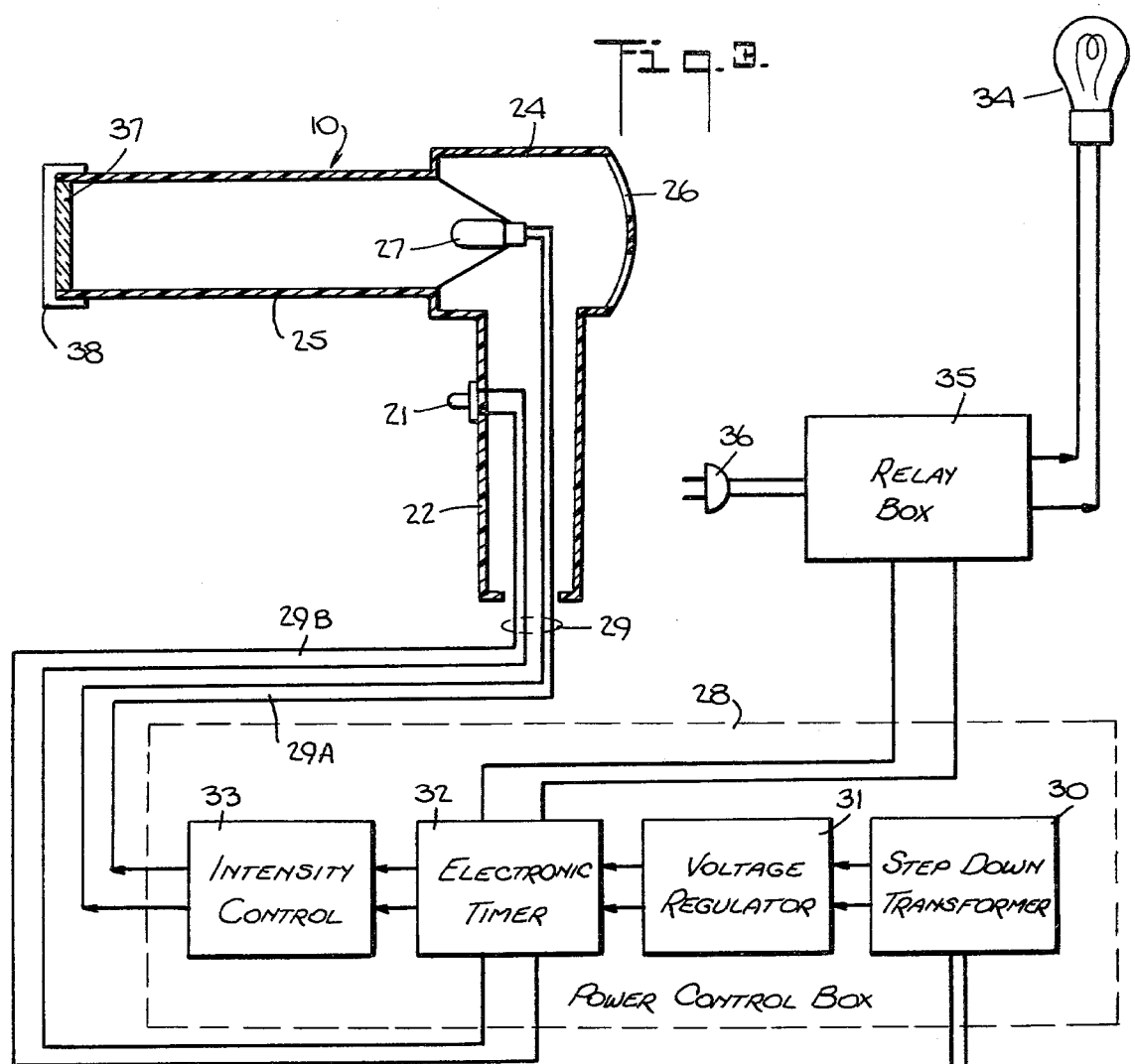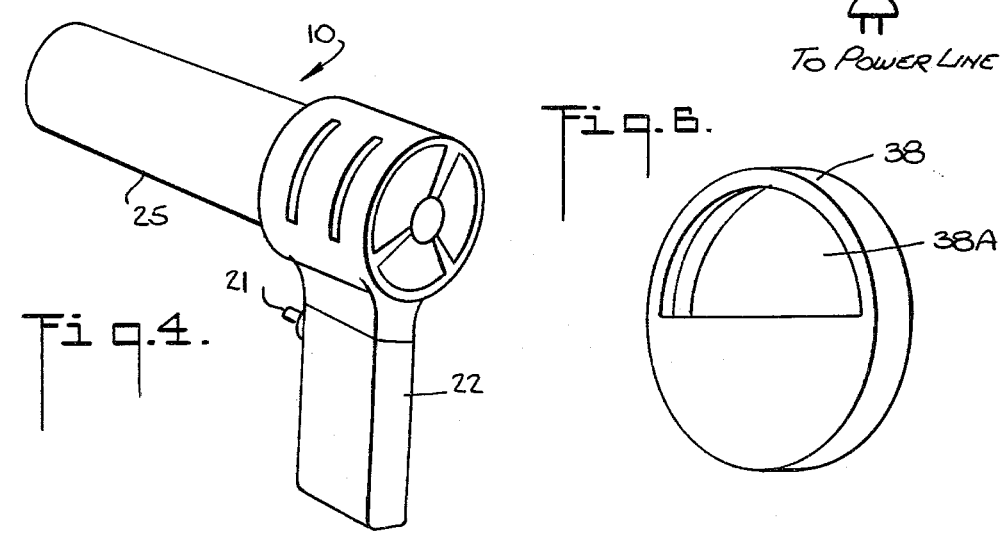

TRANSILLUMINATION DIAGNOSTIC SYSTEM

BACKGROUND OF INVENTION

1. Field of Invention

This invention relates generally to transillumination techniques for examining the morphology of human organs, and more particularly to a diaphanoscopic system adapted to carry out breast examinations and constituted by a portable light-beam projector of controllable intensity and limited duration operating in conjunction with a camera assembly to produce chromatic diaphanographs useful for diagnosis.

2. Prior Art

An elementary and well-known form of transillumination is candling in which an egg or other relatively translucent article is examined by being held between a light source and the eye of the observer. Portions of the human anatomy are more or less permeable to light rays, and it is known that by detecting the amount of light passing through an anatomical region of interest, a physician or trained observer can learn about the morphology thereof.

In its medical applications, transillumination or diaphanoscopic examination is presently employed in studying sinus cavities, the scrotum and fluid cavities in the head. Transillumination is of particular value in detecting and diagnosing the onset of hydrocephalus, which involves an abnormal increase in the amount of cerebrospinal fluid within the cranial cavity. This condition, which is not uncommon in premature infants, is characterized by the expansion of the cerebral ventricles accompanied in some instances by enlargement of the skull and the resultant atrophy of the brain. Because there is a distinct possibility that mental retardation will result from hydrocephalus, early detection of this condition is desirable so that appropriate corrective measures can be taken.

The Johnson U.S. Pat. No. 3,674,008 and the Thomas U.S. Pat. No. 3,527,932 describe the clinical procedure for diagnosing hydrocephalus by transillumination. In this technique, a flashlight is placed against the infant's skull, the remainder of the skull being examined by the physician for light transmission. For a normal skull with the fluid within the cranial cavity at a normal level, the skull will be relatively opaque and little light will pass therethrough. If, however, there is a large quantity of fluid in the immediate vicinity of the light source, the skull will then be fairly translucent so that the light can be seen by the observer. Other prior art patents of interest which relate to transillumination are the Schwartz U.S. Pat. No. 2,161,688 and the Goldman U.S. Pat. No. 3,769,963.

While it will be recognized that a system in accordance with the present invention has many other medical applications for morphological diagnosis, the primary concern of the present invention is with transillumination for breast examination, particularly in connection with the diagnosis of mammary carcinoma; for the incidence of such cancer appears to be on the rise, at least in the United States, and early detection thereof is highly desirable. Because the most commonly used technique for breast examination is radiology, and there is a growing public alarm with adverse effects that may result from exposure to X-rays, the need now exists for a diagnostic procedure that is simple, effective and yet altogether innocuous.

The three most widely used clinical techniques for mammary examination are thermography, radiology and ultrasonography. Thermography, which detects infra-red emission from the internal structure of the region under examination, is now frequently employed in the diagnosis of mammary carcinoma, for it is an inexpensive procedure and perfectly safe. Thermography reveals functional and metabolic alterations, the presence of a malignant tumor being detected by reason of its thermogenic power.

However, the margin of error with thermography is fairly high because of so-called false positives and negatives. An internal nodule which emits a relatively large amount of infra-red energy is generally identified as a carcinoma and may be identified as such by thermographic examination. But the nodule having such thermal properties may in fact not be a carcinoma, as evidenced by X-ray or other techniques, and therefore in thermography represents "a false positive." On the other hand, a nodule which exhibits a low level of thermogenic power may be dismissed by thermographic examination and yet prove to be a "cold" carcinoma, this being characterized as "a false negative."

Apart from the hazards of radiation exposure which are an inevitable concomitant of radiological examination, the record produced thereby has distinct limitations, for it is constituted by a black and white shadowgraph whose pattern is determined by the relative permeability of internal structure to X-rays. Thus fatty tissue is effectively transparent to X-rays, whereas a malignant tumor is relatively opaque, while other physiological elements are more or less opaque. Hence the resultant shadowgraph reveals the irradiated internal structure in terms of gray scale graduations whose proper interpretation requires a high order of skill and experience on the part of the radiologist.

Ultra-sonography, which explores internal structure by means of a scanning beam of ultrasonic energy in a pulse echo technique, depends on the degree to which structural elements in the path of the beam absorb or reflect this energy. Ultra-sonography also has inherent limitations, for certain internal elements may differ physiologically or pathologically and yet possess virtually the same properties with respect to the ultrasonic beam. Hence differences which may be significant medically are not made evident by this technique.

Though transillumination for the detection of hydrocephalus is a widely used technique, in the field of mammary examination its clinical applications have heretofore been much more limited because of certain practical considerations which will later be analyzed. The medical literature in this field is, therefore, relatively scanty. Among the few published articles is that by Gros et al. in J. Radio. Electrol. 53, 297–1972, "Diaphanologie Mammarie."

Yet, as pointed out recently by DiMaggio et al. of the Institute of Radiology of Padua University of Italy in the June 1978 issue of Senologia (page 69 et seq.) in an article entitled "Diaphanoscopic Study of Dystrophic Alterations of the Breast," the transillumination technique is highly useful in mammary examination, particularly if used to complement better known techniques such as radiological observation; for what may fail to show up in one technique may in many instances be made evident by the other.

The authors of this article report the results obtained from the diaphanoscopic mammary examination of several thousand women. The conclusion reached is that this technique makes it possible to find lesions in fibrous mamma, to discover the presence of papillomas, even where there is no secretion of the manilla, and to locate opaque nodules which are "suspect." Moreover, with transillumination, one can, according to this article, obtain a correct reading of the cystic nature of hyper-transparent nodules as well as a correct reading of sclerocystic regions. Also, it becomes possible in cases of normotransparent dystrophic areas, to remove the suspicion of cancer as to these areas.

Hence with transillumination, even if one does not exclusively rely on this technique in breast examination, it nevertheless constitutes a valuable adjunct in resolving ambiguities and reducing errors arising in radiological thermographic or other techniques with which the medical profession is presently more conversant.

As distinguished from the radiological technique which merely produces a gray scale shadow of irradiated internal structure, mammary transillumination affords information regarding the observed internal structure in terms of color. When a beam of light is projected through a mammary protuberance and the placement of the beam is such as to pass through fatty tissue, its appearance to the eye of the observer is reddish-orange, whereas vascularization is presented as black striae.

The presence of fibro-glandular tissue which is developed during pregnancy and breast feeding is made apparent by its high degree of opacity. The appearance of cysts in diaphanoscopic examination depends on their content. Thus cysts with a clear content have the same color as their background if they are surrounded by fatty tissue, but they are visible as areas with a somewhat higher transparency if surrounded by less transparent areas because of an intense fibro-glandular proliferation. Cysts with a brownish, cloudy or blue content are distinguishable in terms of color and relative opacity from those with a hematic content.

Thus in transillumination of the breast, the distinguishing features of the internal structure are expressed both chromatically and in terms of relative opacity to light, thereby affording more detailed data than is obtainable with prior techniques.

To take full advantage of transillumination, the requirements which are imposed on the light source are somewhat contradictory. Thus the white light beam must be sufficiently intense and concentrated to permit breast analysis, even with breasts which are highly light-absorbent. On the other hand, the beam must not be so intense as to result in uncomfortable overheating of the breast, with possibly damaging effects.

Moreover, it is not sufficient that the light intensity be such as to render the internal structure visible to an examinining physician, for it must be adequate to permit the taking of photographs. It must be borne in mind that photographic film responds photochemically to light and has a more marked response to so-called actinic rays. Actinic rays refer to that portion of the light spectrum that is rich in green, blue, violet and ultraviolet rays.

Inasmuch as a breast under transillumination is predominantly reddish-orange in coloration, even when irradiated by an intense white light it produces a somewhat dim image in colors with respect to which photographic film has a relatively poor response. These factors create difficulties in the taking of color photographs, particularly of the "instant" film type.

In taking a color photograph of a transilluminated breast, this must be done in a darkened room so that ambient light does not interfere with the low-level light emitted from the breast and the only light incident to the camera lens are rays arising from the breast. And the picture cannot have an unduly long time exposure, for the examining physician who is manipulating the light beam with respect to the breast protuberance must be in a position to snap a picture as soon as he observes internal structure of interest. Thus a flashlight-produced beam, which is adequate in skull examination, is totally unsuitable for breast examination.

Another factor that must be taken into account is the danger of electrical shock. To generate a light-beam of adequate intensity, use must be made of a high wattage lamp powered from the standard a-c line rather than by low voltage batteries. For breast examination, the light-beam source must be portable in nature so that it can be manipulated and oriented with reference to the breast. Since the lamp necessarily has a power cable leading thereto, this could be hazardous both to the doctor and the patient if the cable carries a high voltage and the lamp housing is of electrically-conductive material. This may be necessary to dissipate the heat generated by the high-wattage lamp; for with an incandescent lamp, a substantial portion of the applied electrical energy is converted into heat.

Still another factor which comes into play in breast examination is the facility in which the examination is conducted. Where the facility is a well-staffed clinic with doctors, nurses and other attendants, then it is possible for, say, one nurse to manipulate a light-beam source with respect to the breast under the direction of the examining physician, while another nurse or paramedical assistant operates a camera and by means of a range finder, focuses onto the breast under examination and takes a picture when instructed to do so by the physician.

But the profession of medicine, at least in the United States and in many European countries, is largely a private practice. The typical patient who is concerned about the condition of her breasts will therefore consult a doctor in his office. This doctor usually has no more than one assistant and has little time to spare in setting up for a breast examination. Ideally, the nature of the transillumination equipment available to the doctor should be such that he is able to carry out an examination and take photographs in a matter of minutes without an elaborate procedure requiring trained assistants. However, existing transillumination equipment for this purpose falls far short of this ideal.

SUMMARY OF INVENTION

In view of the foregoing, the principal object of the invention is to provide a transillumination diagnostic system adapted to carry out breast examination without any danger to the patient and constituted by a portable light-beam projector operable in conjunction with a camera assembly to produce diaphanographs in which the internal structure of interest is clearly delineated in chromatic terms as well as in graduations in light intensity.

A significant advantage of a portable light-beam projector in accordance with the invention is that it makes use of a low-voltage, high-wattage quartz-halogen lamp to produce a high intensity white light beam, the lamp being powered through an extensible cable leading to a control box connected to the standard high-voltage a-c line, so that the patient and operator are subject only to a relatively low, non-hazardous voltage. The control box, which isolates the operator and patient from high voltage, functions to supply to the lamp a regulated low voltage of adjustable magnitude for a timed interval (i.e., 15 seconds) whereby the intensity of the beam may be set to a desired level and the light beam which is projected through the breast when the projector is triggered, is automatically cut off at the conclusion of the time interval to prevent overheating of the breast.

Also an object of the invention is to provide a light-beam projector in the form of a gun from whose barrel the beam is projected, the gun grip having a trigger-finger switch to operate the reflector lamp whose rim is sealed to the edge of the barrel to confine the rays thereto.

A salient feature of the invention resides in a relay box associated with the projection lamp control box which acts to control the supply of current to an examination room lamp whereby when the trigger finger switch of the gun is activated to project the transillumination light beam, the examination room lamp is simultaneously cut off to darken the examination room, the examination room lamp being automatically reactivated at the conclusion of the examination time interval, thereby facilitating the examination procedure.

Yet another object of the invention is to provide a camera assembly in which the camera is supported at one end of a tripod-mounted bracket whose other end terminates in a guide fixture on which the camera lens is pre-focused, the guide fixture being adapted to engage the rib cage of the patient at a point just above the breast to be examined whereby the fixed distance between the camera lens and the breast is maintained throughout the examination to facilitate the taking of properly-focused pictures.

Still another object of the invention is to provide a camera assembly which includes an optical filter in advance of the camera lens to enhance the response of the film to the predominantly orange-red coloration of the light image emitted from the breast.

A further object of this invention is to provide a system of the above type which makes it possible for an examining physician, without difficulty despite the absence of assistance, to orient the light-beam gun with respect to the breast under examination and to observe the transillumination images produced at different beam positions, as well as to take well-focused color pictures of these images without the need to observe them through the camera range finder.

Briefly stated, these objects are attained in a transillumination system in accordance with the invention in which the light source is constituted by a portable light-beam projector in the form of a gun whose slotted, heat-absorbent metal body houses a reflector lamp of the quartz-halogen type, the rim of the reflector being sealed to one end of a metal barrel extending forwardly from the body whereby the light rays from the lamp are confined to the barrel. The other end of the barrel is enclosed by a diffuser plate which prevents the flow of convection currents therefrom and projects a relatively cool beam having a uniform light intensity throughout its cross section, the heat generated by the lamp being absorbed and dissipated by the barrel and by the body.

Extending downwardly from the body of the gun at right angles to the barrel is a hand grip having a trigger-finger switch to control the lamp, a low-voltage power cable being extended from the base of the grip to a control box which is powered from the standard high voltage a-c line. The box includes a step-down transformer to provide a low voltage for the lamp, a voltage regulator to stabilize the low voltage despite fluctuations in the line voltage, and a timer which, when the trigger-finger switch is activated, supplies the low voltage to the lamp for a predetermined interval. Also provided are potentiometer means to adjust the operating level of the voltage to vary the intensity of the beam.

The system further includes a camera assembly constituted by a tripod-mounted bracket having a camera secured to one end which is trained on a guide fixture secured to the other end thereof, the camera lens having a blue optical filter thereover to enhance the sensitivity of the film to rays of the type emitted from a transilluminated breast.

The fixture is adapted to engage the rib cage of the patient just above the breast and thereby present the breast to the camera lens at a fixed focus position. The shutter mechanism of the camera is coupled through a cable to a remote actuator which is operated by one hand or foot of the operator, the camera preferably including automatic film advance means which in the case of an "instant" film camera ejects the exposed film after a picture is taken, and in the case of a conventional camera advances the film to present the lens an unexposed frame thereof for the next picture to be taken.

Thus an operator who holds the light beam projecting gun in his other hand is able without assistance to orient the light beam relative to the patient's breast and to activate the trigger-finger switch for transillumination and observe the internal structure of interest, the operator also being in a position to take a well-focused picture without having to observe the structure of interest through the range finder of the camera.

OUTLINE OF DRAWINGS

For a better understanding of the invention as well as other objects and further features thereof, reference is made to the following detailed description to be read in conjunction with the accompanying drawings, wherein:

FIG. 3 is a sectional view of the light-beam projector gun and a schematic view of the associated power control box and relay box;

FIG. 4 is a perspective view of the light-beam gun;

FIG. 6 is a view of a mask attachable to the barrel of the gun to shape the light-beam projected therefrom.

DESCRIPTION OF INVENTION

General Arrangement

Figure 1:
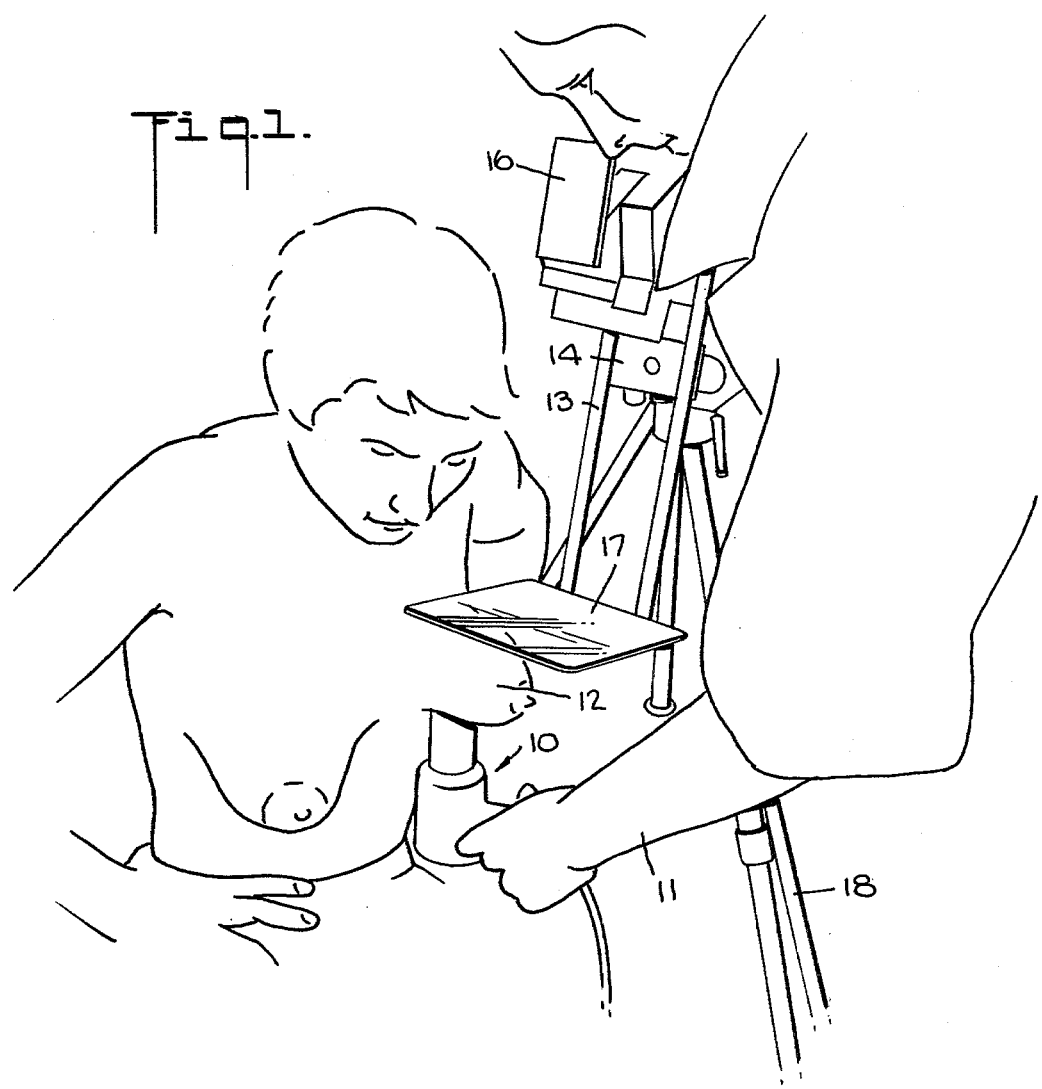
FIG. 1 is a perspective view illustrating a transillumination system in accordance with the invention, the system being shown as it operates to examine the breast of a patient and to take color pictures of transilluminated regions thereof.

Referring now to FIG. 1, there is shown a transillumination diagnostic system in accordance with the invention for breast examination, the system including a light-beam projecting gun 10 whose grip is held in one hand by an examining physician or operator 11 and positioned under and against the breast 12 of the patient being examined so that all rays from the beam penetrate the breast.

The system further includes a camera assembly including a bracket 13 formed by a pair of parallel rails which are bridged by a mounting plate 14 to which a hand grip 15 is attached. Secured to the upper end of bracket 13 is a camera 16 whose lens is trained on a guide fixture 17 connected to the lower end of the bracket. Camera 16 is supported on the swivel head of a tripod 18 making it possible to adjust the angular position and height of the camera to accommodate the assembly to the seated patient. Camera 16 may be any good quality camera capable of taking color pictures and provided with a shutter control mechanism that can be remotely controlled through a cable 19 coupled to an actuator 20 which is installed in grip 15 and is operated by the trigger finger of the holder. Alternately, the actuator may be of the foot pedal type.

Camera 16 is preferably an instant-picture camera such as the Polaroid SX 70 Sonar One-Step Land Camera which is capable of taking good quality color pictures, the exposed film being automatically ejected and developed to provide a positive print after each operation of the shutter mechanism. When a conventional camera is used to take color pictures, the camera is preferably of the type having an automatic film advance mechanism, so that after each shutter operation, the exposed film frame advances to present an unexposed frame to the lens.

Guide fixture 17 in FIG. 1 takes the form of a transparent plate of high grade acrylic material whose sides are contoured to fit against the rib cage of the patient just above the breast. In this way the breast, which is pressed against the underside of the plate by the gun barrel, lies within the field of view of the camera. Since the distance between the guide plate and the camera lens is fixed, once the lens is focused for this distance, there is no further need for focus adjustment from picture to picture.

In the case of a Polaroid camera having a Sonar-type automatic focusing, the lens barrel is automatically brought into focus with the first picture taken, so that with subsequent pictures, no further focusing action occurs, for the lens is already in focus for the fixed distance between the breast and the camera.

Light-beam gun 10 includes a trigger-finger switch 21 mounted on the grip 22 grasped by the hand of the operator. When this switch is operated, an intense white light beam is generated that is projected into the breast to effect transillumination thereof. In order to best view a particular region of the breast, the beam direction should be substantially normal to the region and not at an angle thereto.

Hence the operator, who is in a position to look down guide plate 17, orients with one hand the activated gun with respect to the underside of the breast until he obtains an illuminated image of the region of interest which best reveals the internal structure thereof. As will later be explained in greater detail, the gun is powered through a control box having an adjustable potentiometer for varying the light intensity. Thus the operator must not only find the region of interest, but he must also set the light intensity so as to attain transillumination affording the optimum chromatic and light transmissivity contrast.

The control box energizes the light-beam gun for a predetermined interval which is adequate to permit the operator to make the necessary adjustments and to locate the region of interest, but not long enough to overheat the breast engaged by the gun barrel. In practice, a timed interval of 12 to 15 seconds has been found to satisfy these requirements.

when the operator sees a transilluminated breast image which he finds revealing, he then with the finger of his other hand activates the camera to take a picture thereof. With a Polaroid camera having a cartridge of ten frames, it is possible to take ten instant color pictures of different regions of the breast under examination and thereby provide the examining physician with a detailed record of his examination for purposes of later diagnosis. With a conventional camera, one may produce transparent film slides which may be projected in magnified form on a viewing screen, such enlargements permitting a closer analysis of the breast morphology.

Alternative Camera Assembly

Figure 2:
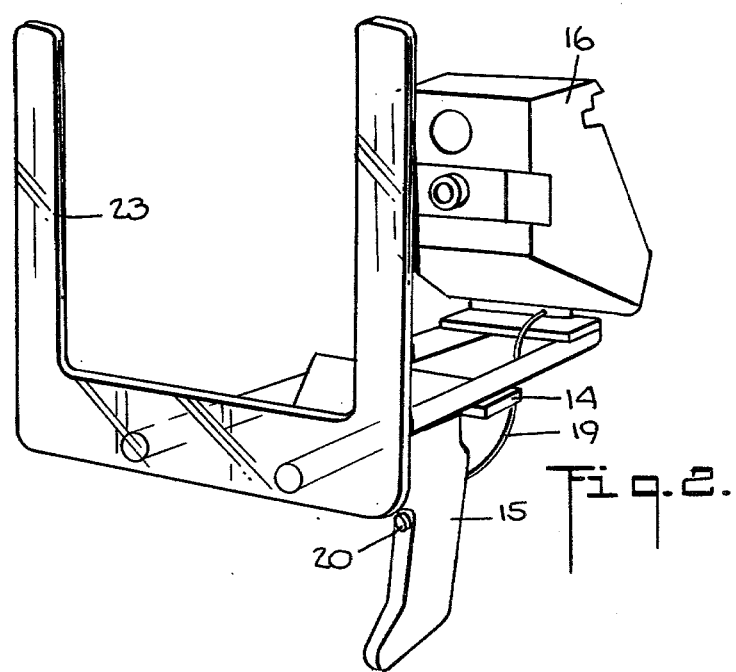
FIG. 2 shows a modified form of camera assembly.

In the assembly shown in FIG. 2, instead of a guide fixture in the form of a transparent plate, the guide fixture 23 in this instance is a bifurcated structure which is adapted to be placed against the patient so that the breast to be examined lies within the opening between the two arms of the fixture. This fixture avoids light reflections from a transparent guide plate and therefore provides somewhat clearer pictures. In all other respects, the examination procedure is the same as that described in connection with FIG. 1.

The Light-Beam Projector and Associated Control Box

Referring now to FIGS. 3 and 4, it will be seen that light-beam projecting gun 10, whose structure is preferably fabricated of aluminum, a light-weight metal of high thermal conductivity, includes a cylindrical body section 24 which is slotted, one end of this section being integral with a cylindrical barrel 25 of smaller diameter which extends axially therefrom. The other end of the body is enclosed by a cap 26 which is provided with arcuate slots for purposes of ventilating the body. Hand grip 22 extends downwardly from body section 24 at right angles to barrel 25.

Housed within body section 24 is a low-voltage, high-wattage incandescent lamp 27 of the reflector type. The rim of the reflector is bonded to the inner end of barrel 25 by epoxy or other suitable sealing agent, so that all light emitted by the lamp is projected through the barrel and no light escapes through the body section.

It is important for purposes of breast trans-illumination that only light visible to the observer and to the camera is that projected through the breast, and that there be no other sources of light in the examination room which would interfere with the examination. It is for this reason that the gun components (body section, barrel and grip) and all finished with a matte-black exterior coating so that there is no perceptible glare from these surfaces. It is also important that when the gun is activated, the examination room like source be turned off so that the examination can take place under darkened conditions, whereby the only light rays visible to the examining physician and the camera are those rays emanating from the transilluminated breast.

Lamp 27 is preferably a halogen-quartz incandescent lamp, such as a Philips #6853 lamp which is a 12-volt, 75-watt lamp having a reflector whose exterior has a black-matte finish.

In the conventional incandescent lamp, the tungsten filament is enclosed within a glass bulb that is evacuated to prevent oxidation of the filament. The evaporation of the filament throughout the life of the lamp, causes blacking of the bulb and thinning of the filament, thereby gradually reducing the light output and resulting in the ultimate failure of the bulb. But in the halogen-quartz lamp, the filament is housed within a small quartz tube filled with an iodine atmosphere whereby the resultant tungsten-iodide lighting source continuously returns evaporated tungsten particles to the filament. As a consequence, the inside wall of the tube does not blacken and the light output remains substantially constant throughout the life of the lamp.

Light-beam projecting gun 10 is operated by a power control box 28 and is coupled thereto by a coiled four-wire flexible cable 29 which is extensible to permit manipulation of the gun with the control box at a fixed position. Since lamp 27 operates at a low voltage (12 V) and power therefor is derived from a standard high voltage a-c power line (110 V or 220 V), the box includes a step-down transformer 30 whose output is applied to a voltage regulator 31 which yields a constant voltage output despite fluctuations in voltage normally encountered in power lines. Since a steady light beam is essential for transillumination, a constant lamp voltage is required for this purpose.

The voltage from regulator 31 is fed through an electronic timer 32 and an intensity control potentiometer 33 control to lamp 27 through double line 29A included in cable 29. Timer 32 is actuated by trigger-finger switch 21 which is connected thereto through the second double line 29B in the cable, the timer serving to supply power to the lamp for a predetermined interval which in practice may be 12 or 15 seconds. The duration of this interval is sufficient to carry out the examination and picture-taking procedure for a selected region of the breast, but short enough to prevent overheating of the breast.

When this procedure is in progress, it is essential that the examination room light source represented by lamp 34 be turned off. For this purpose, electronic timer 32 is also operatively coupled to a relay box 35 interposed between lamp 34 and the power line plug 36 therefor, the arrangement being such that power is normally supplied to lamp 34 and is interrupted by relay 35 only when timer 32 is operative during the timing interval.

In order to obtain a white light beam whose light intensity is substantially uniform throughout its cross-sectional area so that whatever changes in intensity appear in the image derived from transillumination of the breast are the result of variations in opacity attributable to differences in the internal structure of the breast, a light diffusion plate 37 is provided which encloses the free end of gun barrel 25. Plate 37 also functions to prevent the flow of convection currents from the barrel which would otherwise tend to heat the breast.

With large breasts, the full cross-sectional dimension of the beam is used for purpose of transillumination, but with smaller breasts it may be necessary to cover the barrel with an apertured mask in cap form, such as mask 38 shown in FIG. 6 which has a semi-circular opening 38A therein to reduce the cross-sectional dimension of the beam. In practice, other mask opening shapes may be provided to accommodate differently formed breasts.

As pointed out previously, photographic film is highly sensitive to actinic rays and less so with rays from other portions of the light spectrum, whereas the light emitted from the transilluminated breast is predominantly reddish-orange and therefore not actinic in nature. Hence a blue-tinted optical filter (not shown) is placed in advance of the camera lens to enhance the response of the film to the illuminated breast image.

The Actual Equipment

Figure 5:
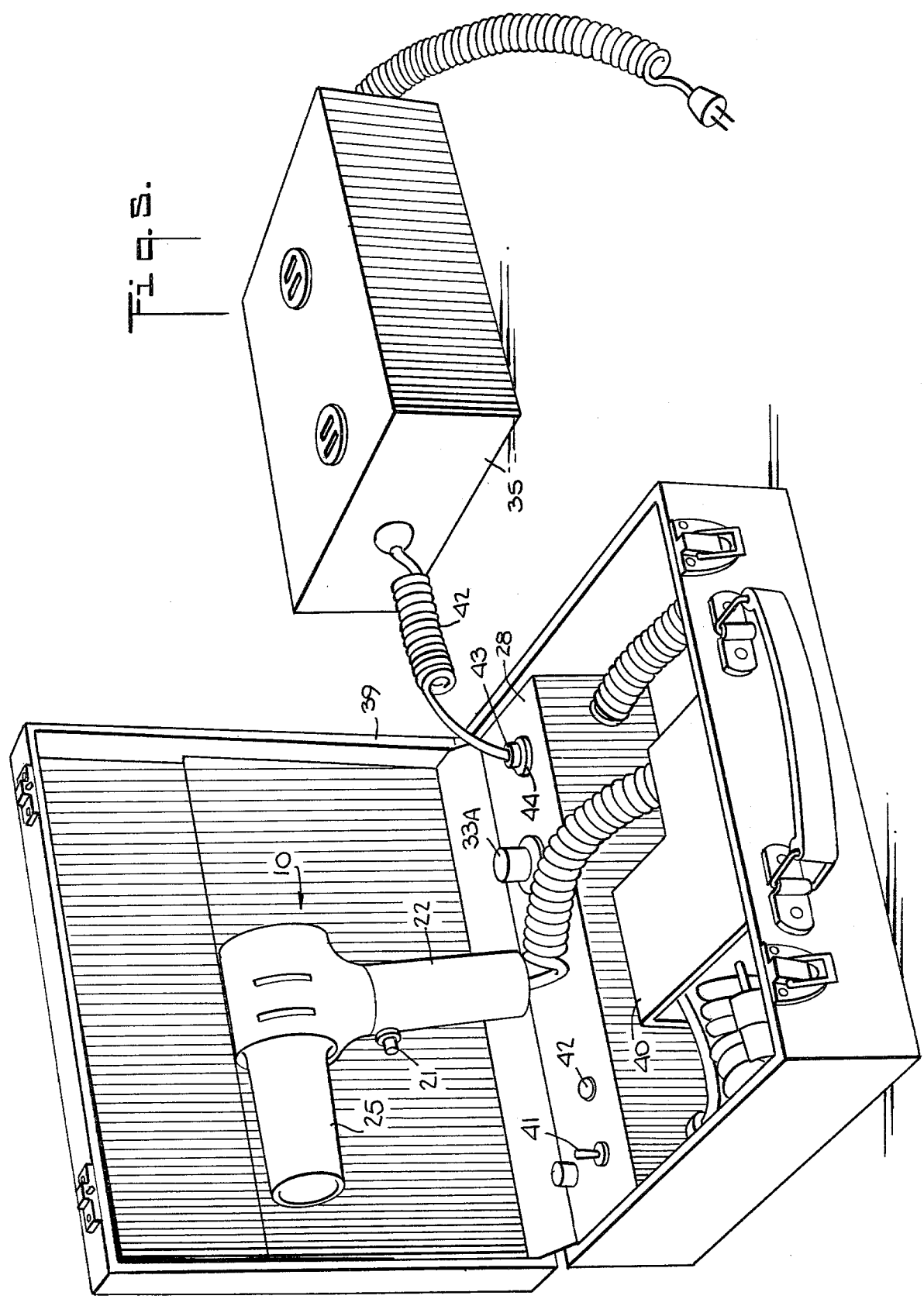
FIG. 5 illustrates an actual embodiment of the attache case which stores the power control box and the light-beam projector, the figure also showing the relay box associated with the control box.

Referring now to FIG. 5, there is shown an actual embodiment of the light beam source in a readily transportable form which is practical for the typical doctor's office or for field use.

It will be seen that control box 28 is housed within an attache case 39 provided with a cushioned socket 40 for light-beam gun 10. Control box 28 is provided with a main power switch 41 and a pilot light 42 to indicate that the power system is activated. Intensity control is effected by potentiometer knob 33A which turns within a circular calibrated scale.

A connection to relay box 35 is effected by a cable 42 having a plug 43 which inserts in a socket 44 in the power control box. In practice relay box 35 may be integrated with control box 28.

Though the invention has been described as a transillumination system for carrying out breast examinations, it will be appreciated that the system by the use of appropriate guide fixtures may be adapted to operated with other portions of the human anatomy.

While there has been shown and described a preferred embodiment of a transillumination diagnostic system in accordance with the invention, it will be appreciated that many changes and modifications may be made therein without, however, departing from the essential spirit thereof. For example, instead of a separate power control box, all the components thereof including the step-down transformer may be incorporated in the hollow grip of the gun with the intensity control knob placed above the trigger-finger switch. Since there is now a high voltage within the grip, the grip is then preferably made of high strength synthetic plastic insulating material.

I claim:

1. A transillumination examination system operable by a single operator for observing a selected portion of the human anatomy, such as the breast, without imparting excessive heat thereto, and for taking pictures of internal regions therein of medical interest, said system comprising:

(A) a light-beam projecting gun having a barrel extending axially from a hollow body section and a grip extending laterally therefrom which is adapted to be held in one hand of the operator, said barrel having a front end and a rear end;

(B) a reflector-type incandescent lamp housed in said body section, the rim of the reflector being sealed to the rear end of the barrel to project light rays through the barrel into the anatomical portion to be transilluminated, the front end of the barrel being covered by a diffuser plate to provide a light beam whose intensity is substantially uniform throughout its cross section, the plate also preventing the flow of convection currents from the barrel which would otherwise tend to heat the anatomical portion, said grip being provided with a trigger-finger switch to activate said lamp;

(C) a power-supply connected to said lamp through said switch and including a timer to energize said lamp upon operation of said switch for a predetermined time interval whose duration is sufficient to carry out an examination procedure but not long enough to overheat the anatomical portion being transilluminated; and (D) a camera assembly constituted by a bracket having at one end thereof a guide fixture adapted to engage the anatomical portion to be examined, and having at the other end thereof a camera whose lens is trained on said guide fixture and is focused on said anatomical portion, said camera having a shutter mechanism which is remotely operated by an actuator whereby the operator who grips the gun in one hand and operates said switch to produce the light beam for transilluminating said anatomical portion, can observe the transilluminated image created at the fixture and take a focused picture thereof by operating the actuator with his other hand or foot.

2. A system as set forth in claim 1, wherein said anatomical portion is a breast and said guide fixture is a transparent plate whose edge engages the rib cage of the patient above the breast, the breast being pressed against the underside of the plate by the barrel of the gun.

3. A system as set forth in claim 1, wherein said lamp is a low-voltage, high-wattage lamp, and said power supply is operated from a standard high-voltage a-c line and includes a step-down transformer to provide a voltage of the appropriate level to the lamp.

4. A system as set forth in claim 3, wherein said lamp is a quartz-halogen lamp.

5. A system as set forth in claim 3, further including an examination room light source and relay means associated with said timer to cut off said light source when said gun is activated.

6. A system as set forth in claim 1, wherein said camera is adapted to take color photographs, and further including an optical filter in advance of said lens to enhance the response of the camera film to a transilluminated image whose light is predominantly non-actinic in nature.

7. A system as set forth in claim 1, further including an apertured mask received over the front end of the barrel and secured thereto to restrict the cross section of the beam.

8. A system as set forth in claim 1, wherein said bracket is mounted on the swivel head of a tripod whereby the assembly is adjustable in angle and height with respect to the anatomical portion under examination, and said actuator is installed on a hand grip attached to said bracket.

* * * * *